(12) United States Patent
Roh

(10) Patent No.: US 10,617,535 B2
(45) Date of Patent: Apr. 14, 2020

(54) SUPPORTING MODULE, MOTION ASSISTANCE APPARATUS INCLUDING THE SUPPORTING MODULE, AND METHOD OF CONTROLLING THE MOTION ASSISTANCE APPARATUS

(71) Applicant: Samsung Electronics Co., Ltd., Suwon-Si, Gyeonggi-Do (KR)

(72) Inventor: Chang Hyun Roh, Seoul (KR)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 968 days.

(21) Appl. No.: 14/603,753

(22) Filed: Jan. 23, 2015

(65) Prior Publication Data
US 2016/0113830 A1    Apr. 28, 2016

(30) Foreign Application Priority Data

Oct. 22, 2014 (KR) .................. 10-2014-0143185

(51) Int. Cl.
| | |
|---|---|
| A61H 1/00 | (2006.01) |
| A61F 2/70 | (2006.01) |
| A61B 5/0488 | (2006.01) |
| A61B 5/22 | (2006.01) |
| A61H 3/00 | (2006.01) |

(Continued)

(52) U.S. Cl.
CPC .............. *A61F 2/70* (2013.01); *A61B 5/0205* (2013.01); *A61B 5/04888* (2013.01); *A61B 5/1121* (2013.01); *A61B 5/224* (2013.01); *A61H 1/0244* (2013.01); *A61H 3/00* (2013.01); *A61H 2003/007* (2013.01); *A61H 2201/1215* (2013.01); *A61H 2201/165* (2013.01); *A61H 2201/5061* (2013.01); *A61H 2201/5079* (2013.01); *A61H 2205/088* (2013.01); *A61H 2230/08* (2013.01); *A61H 2230/25* (2013.01); *A61H 2230/505* (2013.01); *A61H 2230/60* (2013.01)

(58) Field of Classification Search
CPC .............. A61H 1/02; A61H 2001/0207; A61H 2001/0211; A61H 1/0214; A61H 1/0237; A61H 1/024; A61H 1/0244; A61H 2001/0248; A61H 2001/0251
See application file for complete search history.

(56) References Cited

U.S. PATENT DOCUMENTS

| | | | |
|---|---|---|---|
| 8,663,134 B2 | 3/2014 | Takahashi et al. | |
| 9,572,520 B2 * | 2/2017 | Hashimoto | ............ A61H 1/024 |

(Continued)

FOREIGN PATENT DOCUMENTS

| | | |
|---|---|---|
| JP | 1993-329186 | 12/1993 |
| JP | 2003-290302 A | 10/2003 |

(Continued)

*Primary Examiner* — Michael J Tsai
(74) *Attorney, Agent, or Firm* — Harness, Dickey & Pierce, P.L.C.

(57) ABSTRACT

A supporting module, a motion assistance apparatus including the supporting module, and a method of controlling the motion assistance apparatus are provided. The supporting module may include a supporting member configured to enclose at least a portion of a support object, and a sensor module configured to sense information regarding whether the support object is out of a neutral position with respect to the supporting member.

19 Claims, 12 Drawing Sheets

(51) Int. Cl.
   *A61H 1/02*    (2006.01)
   *A61B 5/11*    (2006.01)
   *A61B 5/0205*  (2006.01)

(56) References Cited

U.S. PATENT DOCUMENTS

| | | | |
|---|---|---|---|
| 9,636,270 B2 * | 5/2017 | Miyazawa | A61F 2/68 |
| 9,675,512 B2 * | 6/2017 | Kare | A61H 1/024 |
| 2008/0188907 A1 * | 8/2008 | Aguirre-Ollinger | A61H 1/0237 607/48 |
| 2008/0249438 A1 * | 10/2008 | Agrawal | A61H 1/0237 601/35 |
| 2009/0036815 A1 * | 2/2009 | Ido | A61H 1/0237 602/23 |
| 2009/0298653 A1 | 12/2009 | Rodetsky et al. | |
| 2009/0306548 A1 * | 12/2009 | Bhugra | A61H 1/024 600/587 |
| 2009/0312682 A1 * | 12/2009 | Hirata | A61F 5/0193 602/23 |
| 2014/0288664 A1 * | 9/2014 | Miyazawa | A61F 2/68 623/24 |

FOREIGN PATENT DOCUMENTS

| | | |
|---|---|---|
| KR | 100651638 B1 | 11/2006 |
| KR | 10-2010-0109362 | 10/2010 |
| KR | 10-2012-0042524 | 5/2012 |
| KR | 10-2013-0001663 | 1/2013 |
| KR | 10-2013-0073743 | 7/2013 |

* cited by examiner

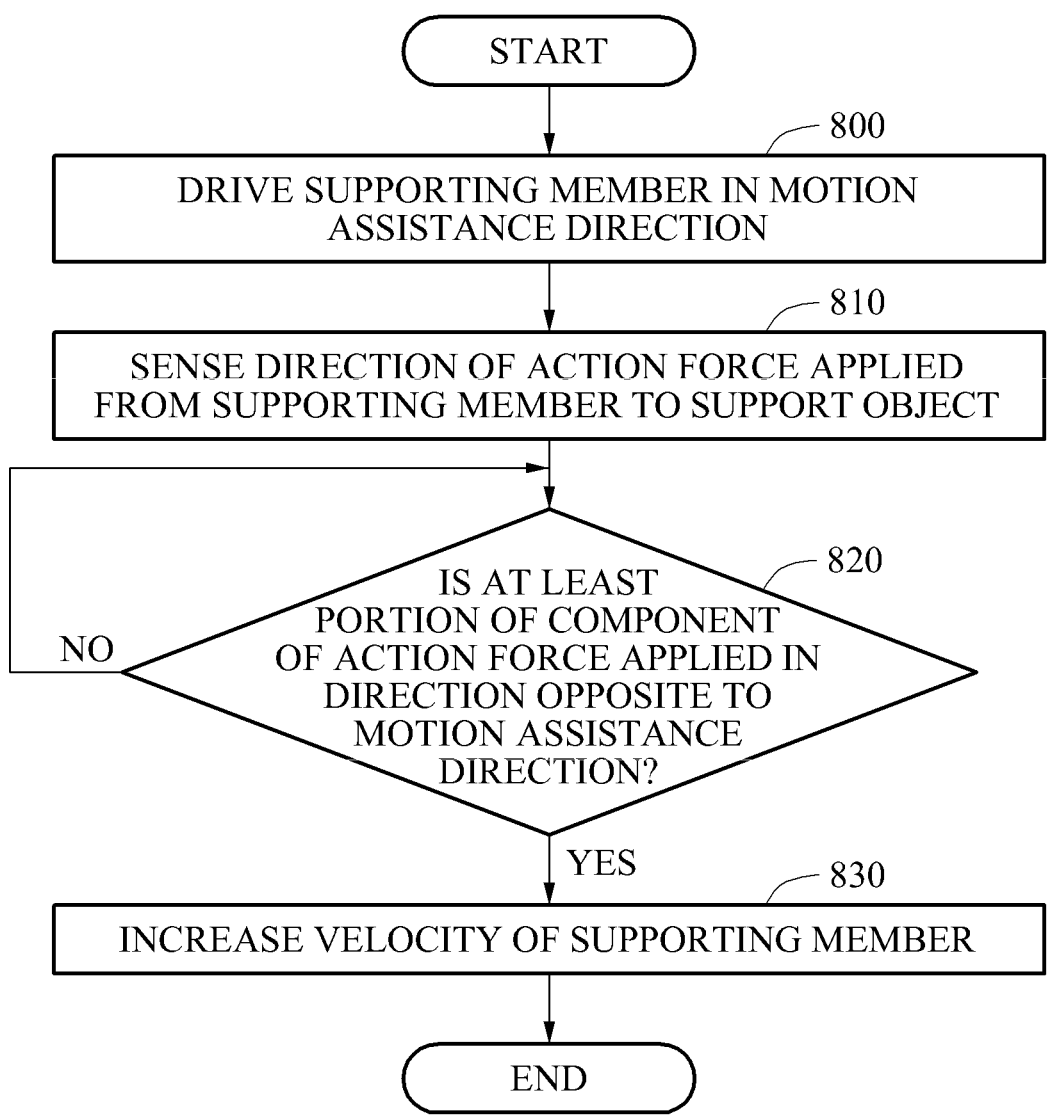

SUPPORTING MODULE, MOTION ASSISTANCE APPARATUS INCLUDING THE SUPPORTING MODULE, AND METHOD OF CONTROLLING THE MOTION ASSISTANCE APPARATUS

CROSS-REFERENCE TO RELATED APPLICATION

This application claims priority under 35 U.S.C. § 119 to Korean Patent Application No. 10-2014-0143185, filed on Oct. 22, 2014, in the Korean Intellectual Property Office, the entire contents of which are incorporated herein by reference in its entirety.

BACKGROUND

1. Field

Example embodiments relate to supporting modules, a motion assistance apparatuses including the supporting module, and/or methods of controlling the motion assistance apparatus.

2. Description of the Related Art

With the onset of rapidly aging societies, many people are experiencing inconvenience and/or pain from joint problems, and interest in motion assistance apparatuses, which enable the elderly or patients with joint problems to walk with less effort, is growing. Furthermore, motion assistance apparatuses for intensifying muscular strength of human bodies may be useful for military purposes.

In general, motion assistance apparatuses for assisting motion of lower parts of bodies may include body frames disposed on trunks of users, pelvic frames coupled to lower sides of the body frames to cover pelvises of the users, femoral frames disposed on thighs of the users, sural frames disposed on calves of the users, and pedial frames disposed on feet of the users. The pelvic frames and the femoral frames may be connected rotatably by hip joint portions, the femoral frames and the sural frames may be connected rotatably by knee joint portions, and the sural frames and the pedial frames may be connected rotatably by ankle joint portions.

SUMMARY

Some example embodiments relate to supporting modules.

According to an example embodiment, the supporting module includes a supporting member configured to cover at least a portion of a support object, and a sensor configured to sense information regarding whether the support object is out of a neutral position with respect to the supporting member.

The information sensed by the sensor may include at least one of a direction of force and torque applied from the support object to the supporting member.

The sensor may be further configured to verify a portion of the supporting member toward which the support object leans.

The sensor may include at least one of a pressure sensor, a temperature sensor, a blood flow sensor, and an electromyography (EMG) sensor.

The sensor may include a pair of pressure sensors facing each other with respect to the support object.

The supporting module may further include a buffering member between the supporting member and the support object.

Some example embodiments relate to motion assistance apparatuses.

According to an example embodiment, the motion assistance apparatus includes a driving source configured to provide power to be used to assist a motion of a user, a supporting member configured to apply force to a support object of the user using power received from the driving source, a sensor configured to sense information regarding whether force is applied to the support object in a direction other than a motion assistance direction, and a controller configured to control the driving source based on the sensed information.

The motion assistance apparatus may further include a power transmitting member configured to transmit power between the driving source and the supporting member, and the sensor may include at least one of a force sensor and a torque sensor, the at least one of a force sensor and a torque sensor being between the supporting member and the power transmitting member.

The sensor may be further configured to verify a portion of the supporting member toward which the support object leans.

The sensor may include at least one of a pressure sensor, a temperature sensor, a blood flow sensor, and an EMG sensor.

The controller may be configured to determine whether the supporting member applies force to the support object in a desired (or alternatively, predetermined) direction, based on the sensed information.

The motion assistance apparatus may further include a power transmitting member configured to transmit power between the driving source and the supporting member, and the sensor may include a torsion sensor on the power transmitting member.

The motion assistance apparatus may further include a power transmitting member configured to transmit power between the driving source and the supporting member, and a portion of the power transmitting member may be disposed on a side surface of a thigh of the user, and another portion of the power transmitting member may be disposed on a front surface of the thigh of the user.

The sensor may include a pressure sensor between the power transmitting member and the supporting member.

Some example embodiments relate to methods of controlling a motion assistance apparatus.

According to an example embodiment, the method of controlling a motion assistance apparatus includes driving a supporting member of a motion assistance apparatus in a desired (or alternatively, predetermined) motion assistance direction to support a support object of a user, sensing a direction of action force applied from the supporting member to the support object, and increasing a velocity of the supporting member when at least a portion of a component of the action force is applied in a direction opposite to the desired (or alternatively, predetermined) motion assistance direction.

The method may further include determining whether a magnitude of the action force exceeds a first value, and the increasing may be performed when the magnitude of the action force is determined to exceed the first value.

The method may further include determining whether a magnitude of the action force exceeds a second value, and the increasing may include gradually increasing the velocity of the supporting member until the magnitude of the action force reaches the second value.

The sensing may be performed based on information sensed by a pair of pressure sensors disposed on the supporting member, the pair of pressure sensors facing each other with respect to the object of the user, and the increasing may include providing, to the supporting member, torque proportional to a difference between two pressure values sensed by the pair of pressure sensors, respectively.

The sensing may be performed based on information sensed by a sensor provided on one side of the supporting member, and the sensor may include at least one of a force/torque (F/T) sensor, a force sensor, a torque sensor, a pressure sensor, a torsion sensor, a temperature sensor, a blood flow sensor, and an EMG sensor Some example embodiments relate to methods of controlling a motion assistance apparatus.

According to an example embodiment, the method of controlling a motion assistance apparatus includes driving a supporting member configured to support a support object of a user in a desired (or alternatively, predetermined) motion assistance direction, sensing information regarding whether force is applied to the support object in a direction other than the motion assistance direction, and increasing a velocity of the supporting member in a direction in which the force applied in the direction other than the motion assistance direction is offset.

The sensing may be performed based on information sensed by a sensor provided on the supporting member (e.g., on one side of the supporting member), and the sensor may include at least one of an F/T sensor, a force sensor, a torque sensor, a pressure sensor, a torsion sensor, a temperature sensor, a blood flow sensor, and an EMG sensor.

Additional aspects of example embodiments will be set forth in part in the description which follows and, in part, will be apparent from the description, or may be learned by practice of the disclosure.

BRIEF DESCRIPTION OF THE DRAWINGS

These and/or other aspects will become apparent and more readily appreciated from the following description of example embodiments, taken in conjunction with the accompanying drawings of which:

FIG. 6 is a flowchart illustrating a method of controlling a motion assistance apparatus according to an example embodiment;

DETAILED DESCRIPTION

Figure 1:
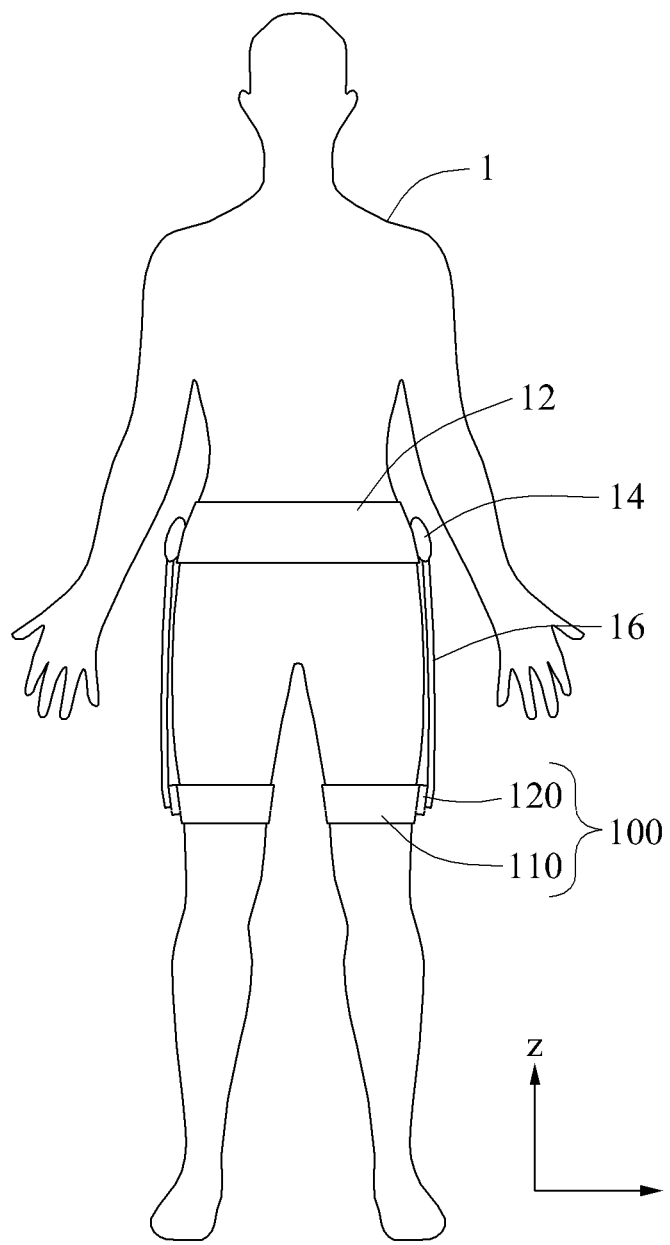
FIG. 1 is a front view illustrating a motion assistance apparatus worn by a user according to an example embodiment.

Hereinafter, some example embodiments will be described in detail with reference to the accompanying drawings. Regarding the reference numerals assigned to the elements in the drawings, it should be noted that like elements will be designated by like reference numerals, wherever possible, even though they are shown in different drawings. Also, in the description of the example embodiments, detailed description of well-known related structures or functions will be omitted.

It should be understood, however, that there is no intent to limit this disclosure to the particular example embodiments disclosed. On the contrary, the example embodiments are to cover all modifications, equivalents, and alternatives falling within the scope of example embodiments.

In addition, terms such as first, second, A, B, (a), (b), and the like may be used herein to describe components. Each of these terminologies is not used to define an essence, order or sequence of a corresponding component but is used merely to distinguish the corresponding component from other component(s). It should be noted that if it is described in the specification that one component is "connected", "coupled", or "joined" to another component, a third component may be "connected", "coupled", and "joined" between the first and second components, although the first component may be directly connected, coupled or joined to the second component.

The terminology used herein is for the purpose of describing particular example embodiments only and is not intended to be limiting. As used herein, the singular forms "a," "an," and "the," are intended to include the plural forms as well, unless the context clearly indicates otherwise. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Various example embodiments will now be described more fully with reference to the accompanying drawings in which some example embodiments are shown. In the drawings, the thicknesses of layers and regions are exaggerated for clarity.

Figure 2:
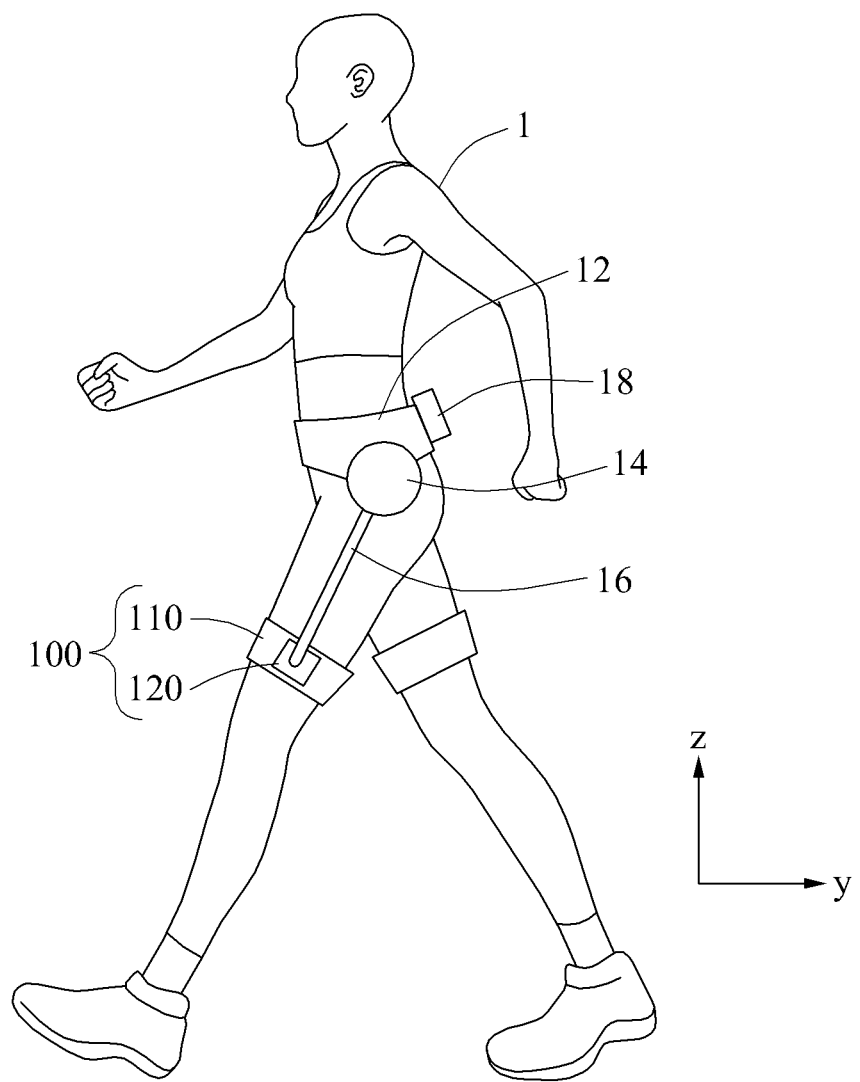
FIG. 2 is a side view illustrating a motion assistance apparatus worn by a user according to an example embodiment.
Figure 3:
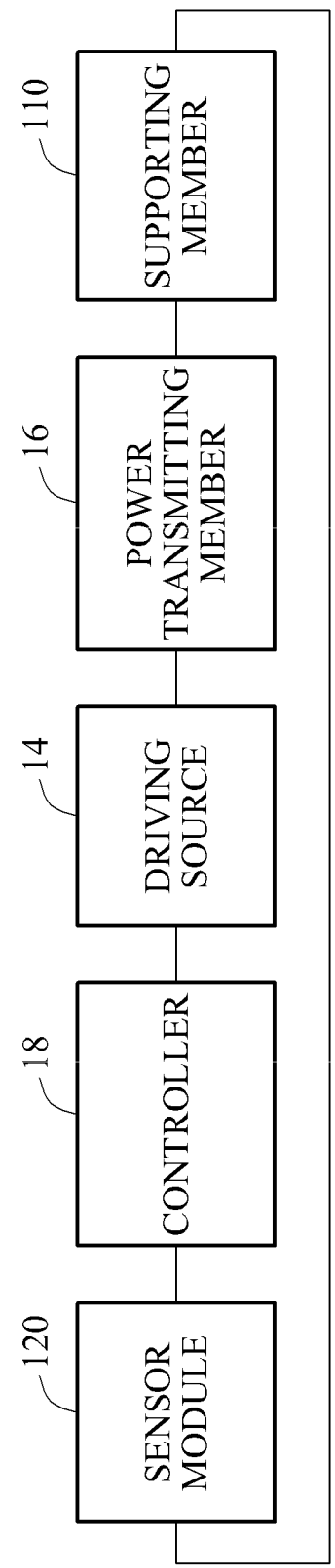
FIG. 3 is a block diagram illustrating a motion assistance apparatus according to an example embodiment.
Figure 4:
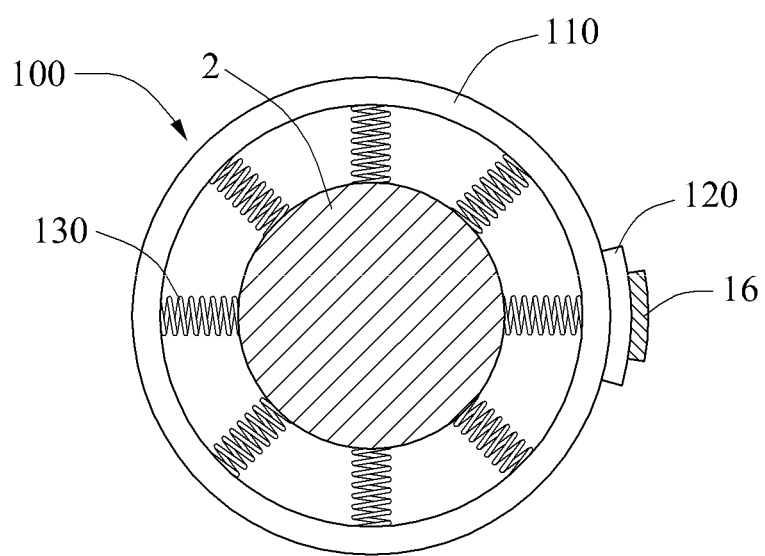
FIG. 4 is a plan view illustrating a supporting module according to an example embodiment.

FIG. 1 is a front view illustrating a motion assistance apparatus 10 worn by a user 1 according to an example embodiment, and FIG. 2 is a side view illustrating the motion assistance apparatus 10 worn by the user 1 according to an example embodiment. FIG. 3 is a block diagram illustrating the motion assistance apparatus 10 according to an example embodiment. FIG. 4 is a plan view illustrating a supporting module 100 according to an example embodiment.

Referring to FIGS. 1 through 4, the motion assistance apparatus 10 may be worn by the user 1 and assist a motion of the user 1. The user 1 may be a human, an animal, or a robot. However, example embodiments are not limited thereto. Although FIGS. 1 and 2 illustrate a case in which the motion assistance apparatus 10 assists a motion of a thigh of the user 1, the motion assistance apparatus 10 may also assist a motion of another part of an upper body, for example, a hand, an upper arm, and a lower arm of the user 1, or a motion of another part of a lower body, for example, a foot, and a calf of the user 1. The motion assistance apparatus 10 may assist a motion of a part of the user 1. The part of the user 1, a motion of which is to be assisted may be referred to as a support object. Hereinafter, a case in which the motion assistance apparatus 10 assists a motion of a thigh of a human will be described.

The motion assistance apparatus 10 may include a fixing module 12, a driving source 14, a power transmitting member 16, a controller 18, and the supporting module 100.

The fixing module 12 may be attached to a portion of the user 1, for example, a waist of the user 1. The fixing module 12 may be in contact with at least a portion of an outer surface of the user 1. The fixing module 12 may cover the outer surface of the user 1.

The driving source 14 may be provided on the fixing module 12. The driving source 14 may provide power to be transmitted to the power transmitting member 16. For example, a plurality of driving sources 14 may be provided. The driving sources 14 may be provided on both sides of the fixing module 12, respectively. However, a number or positions of the driving sources 14 are not limited thereto.

The power transmitting member 16 may be connected between the driving source 14 and the supporting module 100. The power transmitting member 16 may transmit power received from the driving source 14 to the supporting module 100. For example, the power transmitting member 16 may be a longitudinal member such as a frame, a wire, a cable, a string, a rubber band, a spring, a belt, and a chain, for example. However, example embodiments are not limited thereto.

The supporting module 100 may support a support object 2 of the user 1, for example, a thigh of the user 1. The supporting module 100 may include a supporting member 110, a sensor module 120, and a buffering member 130.

The supporting member 110 may be disposed to cover or enclose at least a portion of the support object 2. The supporting member 110 may apply force to the support object 2 using power received from the power transmitting member 16.

The sensor module 120 may sense whether the support object 2 is out of a neutral position with respect to the supporting member 110. The sensor module 120 may sense information about a relative motion of the support object 2 with respect to the supporting member 110. The sensor module 120 may verify a portion of the supporting member 110 toward which the support object 2 leans. For example, the sensor module 120 may sense a direction of force or torque applied from the support object 2 to the supporting member 110. The sensor module 120 may be disposed between the supporting member 110 and the power transmitting member 16. For example, the sensor module 120 may include a force sensor, a torque sensor, and a force/torque (F/T) sensor configured to sense force and torque in six axial directions simultaneously.

The buffering member 130 may be disposed between the supporting member 110 and the support object 2, and configured to buffer resistance between the supporting member 110 and the support object 2. The buffering member 130 may include an elastic body such as, sponge, Styrofoam, and a spring, for example. The buffering member 130 may be omitted, as necessary.

The controller 18 may control the driving source 14 based on information sensed by the sensor module 120. When the driving source 14 is controlled, force or torque to be transmitted through the power transmitting member 16 may change. Thus, a velocity of the supporting member 110 may be adjusted. The velocity of the supporting member 110 may increase or decrease to mitigate or prevent application of force interfering with a motion of the support object 2.

FIGS. 5A through 5D are plan views illustrating an operation of the supporting module 100 according to an example embodiment. In detail, FIGS. 5A through 5D illustrate forces applied between the supporting member 110 and the support object 2 with respect to time while a motion assistance operation is being performed in a direction M.

Figure 5A:
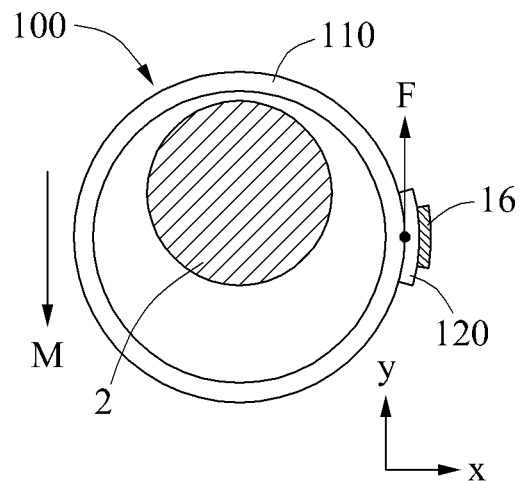
FIGS. 5A through 5D are plan views illustrating an operation of a supporting module according to an example embodiment.

Referring to FIG. 5A, when the motion assistance operation is performed in the desired (or alternatively, predetermined) motion assistance direction M, the supporting member 110 may assist a motion of the support object 2 by moving faster than the support object 2 in the direction M. The supporting member 110 may apply force to the support object 2 in the direction M. In this example, a direction of force applied from the support object 2 to the supporting member 110 may be opposite to the direction M. Thus, a direction of force F sensed by the sensor module 120 may be opposite to the direction M. When the motion assistance direction M of the supporting module 100 is opposite to the direction of the force F sensed by the sensor module 120, a substantial motion assistance operation may be performed.

Figure 5B:
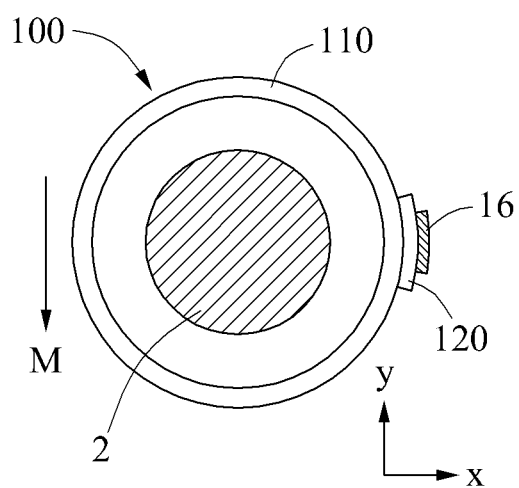

Referring to FIG. 5B, when force is transmitted from the supporting member 110 to the support object 2, the support object 2 may move by inertial force in the motion assistance direction M at a faster velocity than the supporting member 110. Further, when a user moves the support object 2 on his or her own although the support object 2 is not in an inertial state, a state similar to FIG. 5B may occur. In this example, a value of force F sensed by the sensor module 120 may be "0" in theory. When the value of the force F sensed by the sensor module 120 is less than or equal to a desired (or alternatively, predetermined value), a substantial motion assistance operation may not be performed.

Figure 5C:
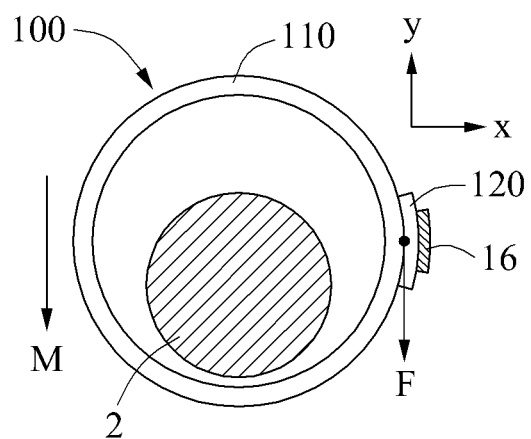

In a state as shown in FIG. 5C, the supporting member 110 may be out of a neutral position and interfere with a movement of the support object 2 in an intended motion direction. The supporting member 110 may apply force to the support object 2 in a direction opposite to the direction M and thus, the user may experience resistance. In this example, a direction of force applied from the support object 2 to the supporting member 110 may be identical to the direction M. Thus, a direction of force F sensed by the sensor module 120 may be identical to the direction M. When the motion assistance direction M of the supporting module 100 is identical to the direction of the force F sensed by the sensor module 120, force interfering with the motion assistance operation may be applied.

Figure 5D:
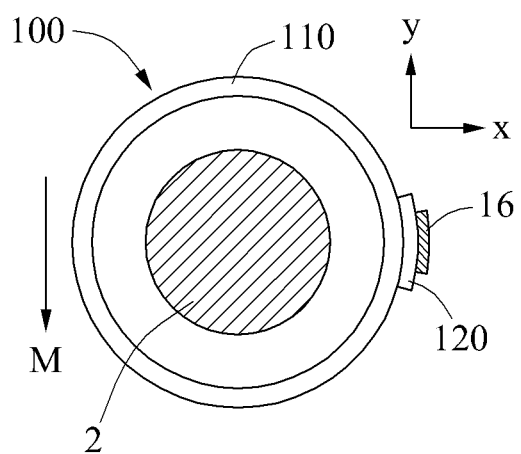

When the state as shown in FIG. 5C is sensed, the controller 18 of FIG. 3 may achieve a state as shown in FIG. 5D by increasing a velocity of the supporting member 110. When the velocity of the supporting member 110 increases, the resistance that the user experiences may decrease.

Figure 7:
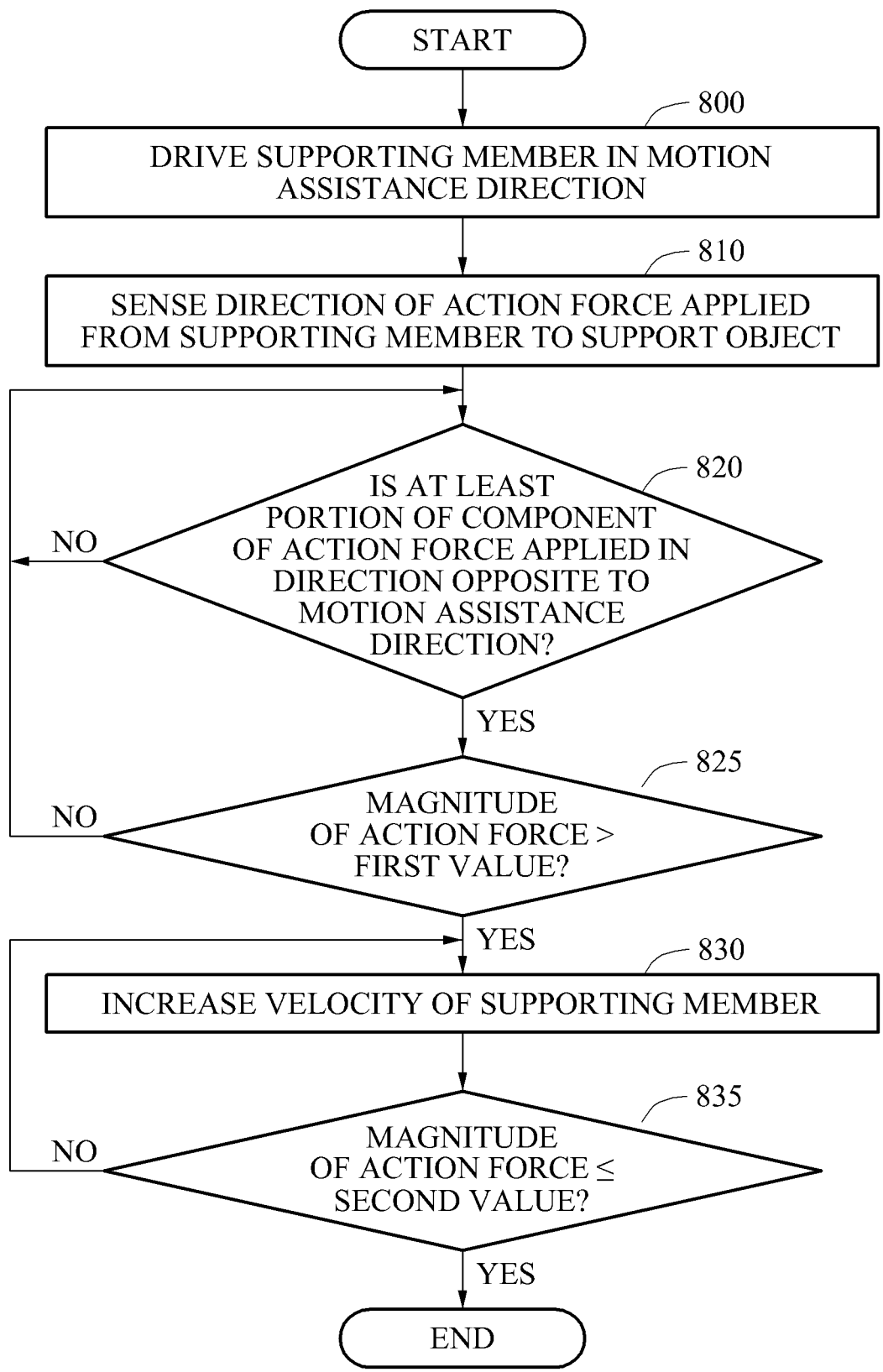
FIG. 7 is a flowchart illustrating a method of controlling a motion assistance apparatus according to an example embodiment.

FIG. 6 is a flowchart illustrating a method of controlling a motion assistance apparatus according to an example embodiment, and FIG. 7 is a flowchart illustrating a method of controlling a motion assistance apparatus according to an example embodiment.

Referring to FIG. 6, the method of controlling a motion assistance apparatus may include operation 800 of driving a supporting member in a motion assistance direction, operation 810 of sensing a direction of action force applied from the supporting member to a support object, operation 820 of determining whether at least a portion of a component of the action force is applied in a direction opposite to the motion assistance direction, and operation 830 of increasing a velocity of the supporting member.

The motion assistance direction may be determined based on a motion assistance state. When the supporting member is driven in the determined motion assistance direction in operation 800, the direction of the action force applied from the supporting member to the support object may be sensed in operation 810.

In some example embodiments, the direction of the action force may be sensed using, for example, a force sensor, a torque sensor, or an F/T sensor disposed between the supporting member and a power transmitting member. In this example, the F/T sensor may be, for example, a sensor configured to sense at least one of force and torque of six axial directions.

In other example embodiments, information regarding a portion of the supporting member toward which the support object leans may be sensed using, for example, at least one pressure sensor, temperature sensor, blood flow sensor, or electromyography (EMG) sensor disposed along a circumference of the supporting member, and the direction of the action force may be determined based on the sensed information.

In operation 820, a controller may determine whether the action force interferes with a motion of the support object in a motion assistance direction. When at least a portion of a component of the action force is applied in a direction opposite to the motion assistance direction, the action force may be determined to interfere with the motion of the support object in the motion assistance direction. When the action force does not interfere with the motion of the support object in the motion assistance direction, operation 820 may be iteratively performed.

When the action force is determined to interfere with the motion of the support object in the motion assistance direction in operation 820, the velocity of the supporting member may be increased in operation 830. When the velocity of the supporting member increases, force applied from the supporting member to the support object in the direction opposite to the motion assistance direction may decrease.

Operation 830 may be performed based on, for example, information sensed by a pair of pressure sensors disposed on the supporting member to face each other with respect to the support object. Operation 830 may include an operation of providing, to the supporting member, torque proportional to a difference between two pressure values sensed by the pair of pressure sensors, respectively.

The method of controlling a motion assistance apparatus may further include, prior to operation 830, operation 825 of determining whether a magnitude of the action force interfering with the motion in the motion assistance direction exceeds a first value. When the magnitude of the action force is determined to not exceed the first value in operation 825, operations 820 and 825 may be iteratively performed.

Operation 825 may mitigate or prevent an undesirable increase in the velocity of the supporting member when resistance is sensed by an error in measurement or when only negligible resistance is present. In operation 825, the velocity of the supporting member may be increased only when the resistance is sufficiently great. Although FIG. 7 illustrates operation 825 performed after operation 820 is performed, operation 825 may be performed prior to operation 820. Detailed descriptions thereof will be omitted for conciseness.

The method of controlling a motion assistance apparatus may further include, after operation 830 is performed, operation 835 of determining whether the magnitude of the action force interfering with the motion in the motion assistance direction is less than or equal to a second value. When the magnitude of the action force is determined to not be less than or equal to the second value in operation 835, operation 830 may be iteratively performed to increase the velocity of the supporting member gradually. By operation 835, the velocity of the supporting member may be increased gradually until the resistance is alleviated sufficiently.

Figure 8:
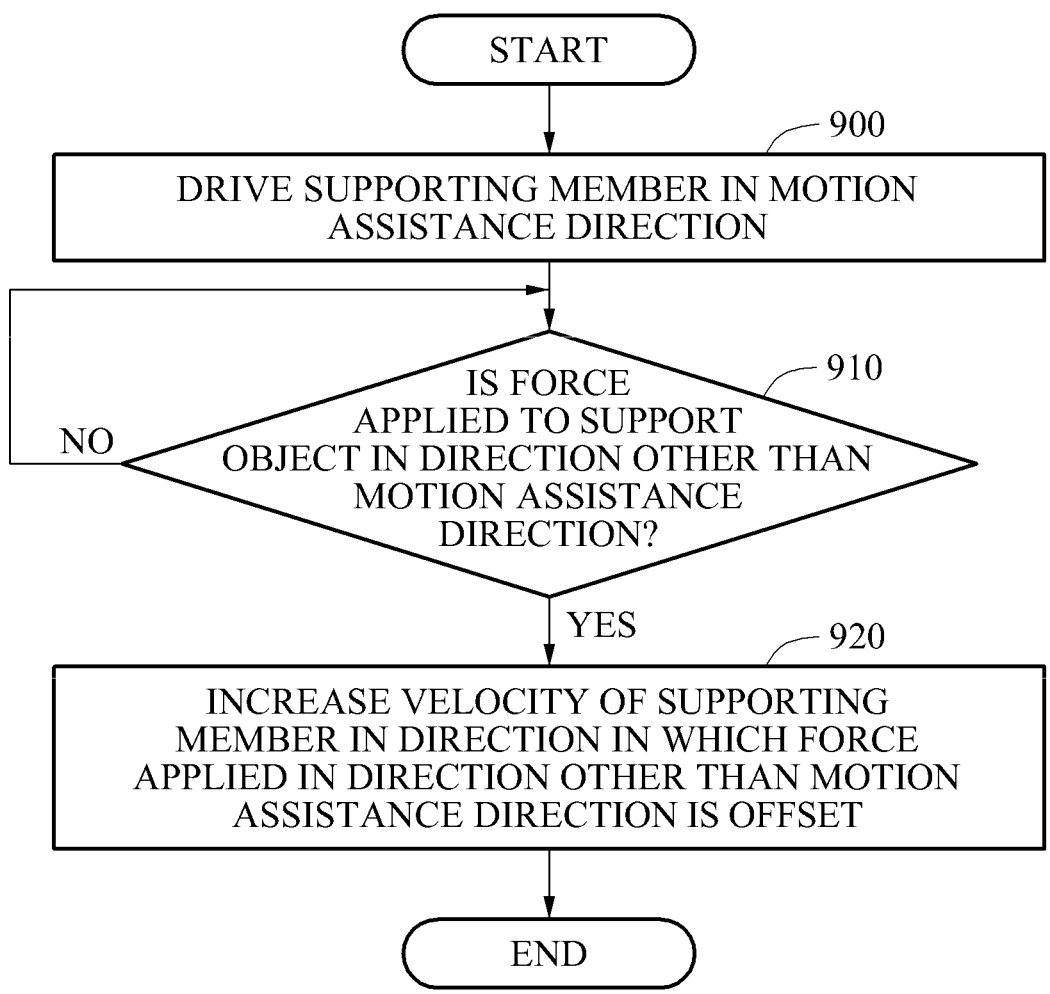
FIG. 8 is a flowchart illustrating a method of controlling a motion assistance apparatus according to an example embodiment.

FIG. 8 is a flowchart illustrating a method of controlling a motion assistance apparatus according to an example embodiment.

Referring to FIG. 8, the method of controlling a motion assistance apparatus may include operation 900 of driving a supporting member in a desired (or alternatively, predetermined) motion assistance direction, operation 910 of determining whether force is applied to a support object in a direction other than the motion assistance direction, and operation 920 of increasing a velocity of the supporting member in a direction in which the force applied in the direction other than the motion assistance direction is offset.

When force is determined to not be applied to the support object in a direction other than the motion assistance direction in operation 910, operation 910 may be iteratively performed.

When force is determined to be applied to the support object in a direction other than the motion assistance direction in operation 910, operation 920 may be performed.

Hereinafter, the same name may be used to describe an element included in the example embodiments described above and an element having a common function. Unless otherwise mentioned, the descriptions on the example embodiments may be applicable to the following example embodiments and thus, duplicated descriptions will be omitted for conciseness.

Figure 9:
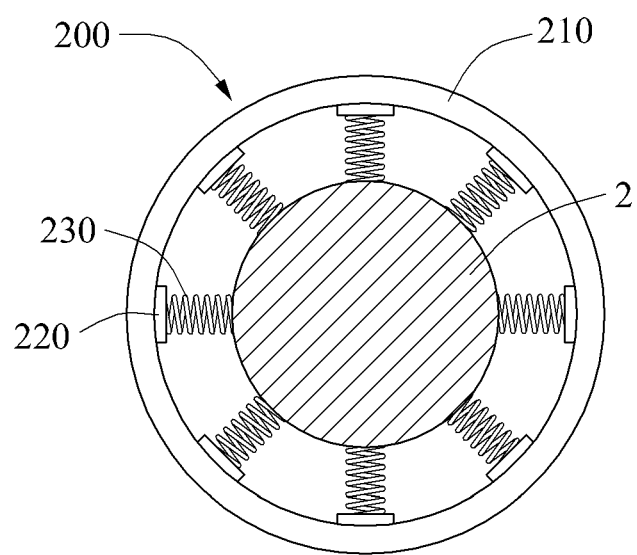
FIG. 9 is a plan view illustrating a supporting module according to an example embodiment.

FIG. 9 is a plan view illustrating a supporting module 200 according to an example embodiment.

Referring to FIG. 9, the supporting module 200 may include a supporting member 210, a sensor module 220, and a buffering member 230.

The sensor module 220 may include a plurality of sensors disposed along a circumference of the supporting member 210. For example, at least one pair of sensors may be disposed to face each other with respect to the support object 2. The plurality of sensors may include pressure sensors, temperature sensors, blood flow sensors, and EMG sensors.

For example, when a plurality of pressure sensors are used, it may be learned that the support object 2 leans toward a sensor sensing a highest pressure, among the plurality of pressure sensors. Similarly, a portion of the supporting member 210 toward which the support object 2 leans may be verified using the temperature sensors, the blood flow sensors, or the EMG sensors.

Figure 10:
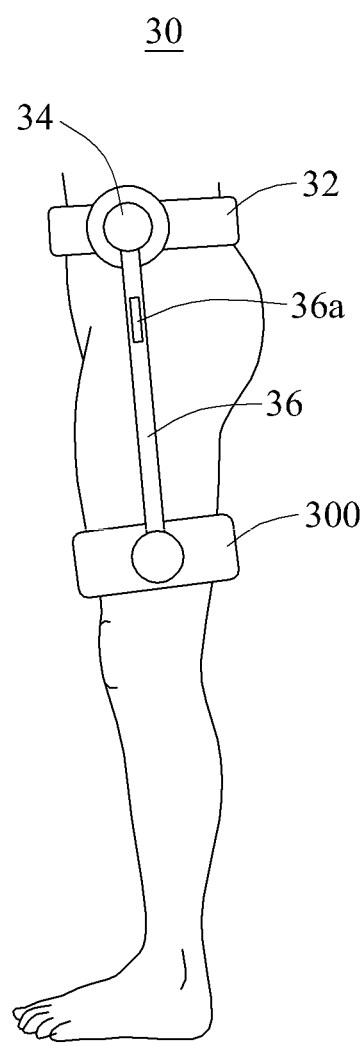
FIG. 10 is a side view illustrating a motion assistance apparatus worn by a user according to an example embodiment.

FIG. 10 is a side view illustrating a motion assistance apparatus worn by a user according to an example embodiment.

Referring to FIG. 10, a motion assistance apparatus 30 may include a fixing module 32, a driving source 34, a power transmitting member 36, a sensor module 36a, and a supporting module 300.

The sensor module 36a may be provided on, for example, the power transmitting member 36. The sensor module 36a may sense whether force is applied to a support object in a direction other than a motion assistance direction, based on a state of the power transmitting member 36.

The sensor module 36a may include, for example, a torsion sensor. By sensing information about a degree of torsion of the power transmitting member 36 using the torsion sensor, whether force is applied to the support object in a direction other than the motion assistance direction may be sensed.

Figure 11:
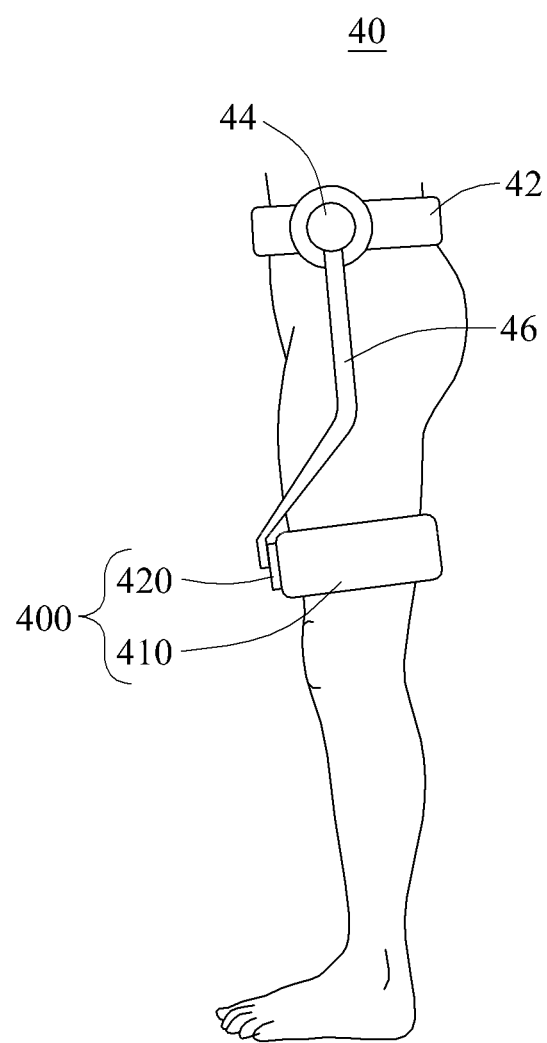
FIG. 11 is a side view illustrating a motion assistance apparatus worn by a user according to an example embodiment.

FIG. 11 is a side view illustrating a motion assistance apparatus worn by a user according to an example embodiment.

Referring to FIG. 11, a motion assistance apparatus 40 may include a fixing module 42, a driving source 44, a power transmitting member 46, and a supporting module 400.

The power transmitting member 46 may be, for example, a frame bent from a side surface of a thigh of a user toward a front surface of the thigh of the user. A portion of the power transmitting member 46 may be disposed on the side surface of the thigh of the user, and another portion of the power transmitting member 46 may be disposed on the front surface of the thigh of the user.

The supporting module 400 may include a supporting member 410, and a sensor module 420. The sensor module 420 may include, for example, a pressure sensor disposed between the power transmitting member 46 and the supporting member 410. By sensing a pressure transmitted from a support object to the supporting member 410 using the pressure sensor, information about force applied in a direction opposite to a motion assistance direction may be sensed.

The controller in this disclosure may include a processor and a memory (not shown). The controller may be an arithmetic logic unit, a digital signal processor, a microcomputer, a field programmable array, a programmable logic unit, a microprocessor or any other device capable of responding to and executing instructions in a defined manner such that the controller is programmed with instructions that configure the processing device as a special purpose computer and is configured to control a driving source based on information sensed by a sensor such that the driving source transmits power to a power transmitting module of the motion assistance apparatus.

The instructions may be stored on a non-transitory computer readable medium. Examples of non-transitory computer-readable media include magnetic media such as hard disks, floppy disks, and magnetic tape; optical media such as CD ROM discs and DVDs; magneto-optical media such as optical discs; and hardware devices that are specially configured to store and perform program instructions, such as read-only memory (ROM), random access memory (RAM), flash memory, and the like. The non-transitory computer-readable media may also be a distributed network, so that the program instructions are stored and executed in a distributed fashion. The program instructions may be executed by one or more processors.

A number of example embodiments have been described above. Nevertheless, it should be understood that various modifications may be made to these example embodiments. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. A supporting module comprising:
   a driver configured to provide power to be used to assist a motion of a user in a motion assistance direction;
   a support configured to apply force to an object of the user in the motion assistance direction by the driver;
   a sensor configured to sense information about a relative motion of the object with respect to the support, and determine an action force direction of action force applied from the support to the object relative to the motion assistance direction in a motion assistance operation; and
   a controller configured to cause the driver to increase a velocity of the support with respect to the object in the motion assistance operation in response to the sensed information indicating that at least a portion of a component of the action force is applied in a first direction opposite to the motion assistance direction in the motion assistance operation,
   wherein the controller is also configured to determine whether a magnitude of the action force interfering with the motion of the user in the motion assistance direction exceeds a first threshold value based on the sensed information, and cause the driver to increase the velocity of the support with respect to the object in response to the magnitude of the action force interfering with motion of the user in the motion assistance direction exceeding the first threshold value.

2. The supporting module of claim 1, wherein the information sensed by the sensor includes at least one of a direction of force and torque applied from the object to the support.

3. The supporting module of claim 1, wherein the sensor is further configured to verify a portion of the support toward which the object leans.

4. The supporting module of claim 3, wherein the sensor comprises a pressure sensor.

5. The supporting module of claim 3, wherein the sensor comprises a pair of pressure sensors facing each other with respect to the object.

6. The supporting module of claim 1, further comprising:
   a buffer between the support and the object.

7. A motion assistance apparatus comprising:
   a driver configured to provide power to be used to assist a motion of a user in a motion assistance direction;
   a support configured to apply force to an object of the user in the motion assistance direction using power received from the driver;
   a sensor configured to sense information about a relative motion of the object with respect to the support and determine an action force direction of action force applied from the support to the object relative to the motion assistance direction in a motion assistance operation; and
   a controller configured to cause the driver to increase the power to be used to assist the motion of the user in the motion assistance operation in response to the sensed information indicating that the action force is in a first direction other than the motion assistance direction in the motion assistance operation,
   wherein the controller is also configured to determine whether a magnitude of the action force interfering with the motion of the user in the motion assistance direction exceeds a first threshold value based on the sensed information, and increase the power provided by the driver in response to the magnitude of the action force interfering with the motion of the user in the motion assistance direction exceeding the first threshold value.

8. The motion assistance apparatus of claim 7, further comprising:
a power transmitter configured to transmit power between the driver and the support, the sensor being interposed between the support and the power transmitter,
wherein the sensor includes at least one of a force sensor or a torque sensor, the at least one of the force sensor or the torque sensor being between the support and the power transmitter.

9. The motion assistance apparatus of claim 7, wherein the sensor is further configured to verify a portion of the support toward which the object leans.

10. The motion assistance apparatus of claim 9, wherein the sensor comprises a pressure sensor.

11. The motion assistance apparatus of claim 7, wherein the controller is configured to determine whether the support applies force to the object in a direction, based on the sensed information.

12. The motion assistance apparatus of claim 7, further comprising:
a power transmitter configured to transmit power between the driver and the support,
wherein the sensor includes a torsion sensor on the power transmitter.

13. The motion assistance apparatus of claim 7, further comprising:
a power transmitter configured to transmit power between the driver and the support,
wherein a portion of the power transmitter is on a side surface of a thigh of the user, and another portion of the power transmitter is on a front surface of the thigh of the user.

14. The motion assistance apparatus of claim 13, wherein the sensor comprises a pressure sensor between the power transmitter and the support.

15. A method of controlling a motion assistance apparatus, the method comprising:
driving a support of the motion assistance apparatus in a motion assistance direction to support an object of a user;
sensing, using a sensor on the support, a relative motion of the object of the user with respect to the support, and determining an action force direction of action force applied from the support to the object of the user relative to the motion assistance direction in a motion assistance operation; and
increasing a velocity of the support with respect to the object of the user in the motion assistance operation in response to the determined action force direction of the action force indicating that at least a portion of a component of the action force is applied in a first direction opposite to the motion assistance direction in the motion assistance operation,
wherein the increasing includes determining whether a magnitude of the action force interfering with a motion of the object of the user in the motion assistance direction exceeds a first threshold value based on results of the sensing, and increasing the velocity of the support in response to the magnitude of the action force interfering with the motion of the user in the motion assistance direction exceeding the first threshold value.

16. The method of claim 15, further comprising:
determining whether a magnitude of the action force exceeds a first value,
wherein the increasing is performed in response to the magnitude of the action force exceeding the first value.

17. The method of claim 15, further comprising:
determining whether a magnitude of the action force exceeds a second value,
wherein the increasing includes gradually increasing the velocity of the support until the magnitude of the action force reaches the second value.

18. The method of claim 15, wherein
the sensing is performed based on information sensed by a pair of pressure sensors on the support, the pair of pressure sensors facing each other with respect to the object of the user, and
the increasing includes providing, to the support, torque proportional to a difference between two pressure values sensed by the pair of pressure sensors, respectively.

19. The method of claim 15, wherein
the sensing is performed based on information sensed by the sensor on one side of the support, and
the sensor includes at least one of a force/torque (F/T) sensor, a force sensor, a torque sensor, a pressure sensor, a torsion sensor.

* * * * *